United States Patent [19]

Itil et al.

[11] 4,089,952

[45] May 16, 1978

[54] NEUROPSYCHOTROPIC AGENTS AND THEIR USE

[75] Inventors: Turan M. Itil, Nyack, N.Y.; Gerhard Laudahn; Werner Martin Herrmann, both of Berlin, Germany

[73] Assignee: Schering Aktiengesellschaft, Berlin and Bergkamen, Germany

[21] Appl. No.: 728,145

[22] Filed: Sep. 30, 1976

[30] Foreign Application Priority Data

Sep. 30, 1975 Germany .............................. 2544061

[51] Int. Cl.² .............................................. A61K 31/56
[52] U.S. Cl. .................................................... 424/243

[58] Field of Search ......................................... 424/243

[56] References Cited

U.S. PATENT DOCUMENTS 4,002,746  1/1977  Hughes et al. .............. 260/239.55 C

*Primary Examiner*—Elbert L. Roberts
*Attorney, Agent, or Firm*—Millen & White

[57] ABSTRACT

Norgestrel, its D- and L-enantiomers and their 17-esters exhibit neuropsychotropic activity when administered in effective dosages to patients exhibiting neuropsychic disturbances of the affective and behavioral type.

6 Claims, No Drawings

NEUROPSYCHOTROPIC AGENTS AND THEIR USE

BACKGROUND OF THE INVENTION

This invention relates to the use of norgestrel, its D- and L-enantiomers and their 17-esters as neuropsychotropic agents and to compositions comprising the L-enantiomer.

Norgestrel (DL-13-ethyl-17α-ethynyl-17β-hydroxy-4-gonen-3-one), its D- and L-enantiomers and their 17-esters are known. See for example, German Pat. Nos. 1,468,604 and 1,493,161.

Several steroids are known to exert depressant effect on the central nervous system and have hypnotic and/or anesthetic effects. These steroids are not useful in accordance with this invention, due to their known side effects, for example, an undesired depression of the central nervous system.

Minor tranquilizers of the benzodiazepine type have become popular as medicinal agents having anxiolytic and sedative activity. However, these active agents have the disadvantage that their use can cause a psychic dependency (WHO Bull. 43 Suppl., 1970: 49). Upon prolonged usage, there is also the danger of tolerance development. Furthermore, the muscle-relaxant properties of these compounds can lead to undesirable side effects (AMA Drug Evaluations, American Medical Assoc. Chicago, 1st ed. [1971]: N 47 et seq.).

Tricyclic neuroleptics are generally known, such as, for example, phenothiazine and the butyrophenones, as medicinal agents having a neuroleptic effect. These compounds result, even in normal doses, in extrapyramidal side effects. As a later consequence, tardive dyskinesia can occur.

It has now been found that norgestrel, its enantiomers and their 17-esters, exhibit a spectrum of activity which is broader than the conventional tranquilizers; more particularly, they possess neuropsychotropic activity of the major tranquilizer type, especially sedative and neuroleptic activity, with the additional advantage that they do not possess the aforementioned side effects.

For examples of other steroids having a broader spectrum of effectiveness, compared to conventional minor tranquilizers, see U.S. Pat. Nos. 3,895,110 and 3,908,007.

SUMMARY OF THE INVENTION

According to this invention, norgestrel (DL-13-ethyl-17α-ethynyl-17β-hydroxy-4-gonen-3-one), its D- or L-enantiomer, or a physiologically acceptable 17-ester thereof, is administered to a patient exhibiting a psychic disturbance in the affective and behavioral ranges, preferably those manifesting sleep disturbances, general restlessness, or states of anxiety, tension and depression in an amount effective to induce a neuropsychotropic effect, thereby producing an ameliorative effect upon said psychic disturbance.

In a composition aspect, this invention relates to pharmaceutical compositions comprising an amount per unit dosage effective to exhibit a neuropsychotropic effect of L-13-ethyl-17α-ethynyl-17β-hydroxy-4-gonen-3-one or a physiologically acceptable 17-ester thereof, in admixture with a pharmaceutically acceptable carrier.

DETAILED DISCUSSION

Any physiologically acceptable 17-ester of norgestrel or its D- or L-enantiomer can be employed. The preferred 17-esters are esters of hydrocarbon carboxylic acids of 1 - 18 carbon atoms, preferably 2 - 8 carbon atoms, e.g., a monobasic alkanoic acid, e.g., formic, acetic, propionic, butyric, isobutyric, α-ethylbutyric, pivalic, valeric, isovaleric, α-ethylvaleric, trimethylacetic, 2-methylbutyric, 3-ethylbutyric, hexanoic, diethylacetic, triethylacetic, enanthic, octanoic, a cyclic acid, preferably a cycloaliphatic acid, e.g., cyclopropylideneacetic, cyclobutylcarboxylic, cyclopentylcarboxylic, cyclopentylacetic, β-cyclopentylpropionic, cyclohexylcarboxylic, cyclohexylacetic, a carbocyclic aryl or an alkaryl acid, e.g., benzoic, 2-, 3- or 4-methylbenzoic acid.

An especially preferred class of esters are those of straight or branched chain monobasic alkanoic acids, preferably 2 - 8 carbon atoms, of which the acetate is most preferred.

Since the exact chemical nature of the acyl radical of the 17-ester group is not critical, as long as it is not physiologically toxic and it can be formed on the 17-hydroxy group, contemplated equivalents of the preferred esters described above, insofar as they can be formed, are those formed with other aliphatic and aromatic unsubstituted and substituted and monobasic, dibasic and polybasic carboxylic acid, saturated or unsaturated aliphatic, araliphatic and aromatic carboxylic acids containing up to 18 and preferably up to 8 carbon atoms, e.g., undecylic, dodecanoic, tetradecanoic, hexadecanoic, octadecanoic, palmitic, β-cyclohexylpropionic acid, 2,3-, 2,4-, 2,5-, 2,6-, 3,4- and 3,5-dimethylbenzoic, ethylbenzoic, 2,4,6-trimethylbenzoic, cinnamic, naphthoic, 3-methyl-α-naphthoic, β-phenylpropionic, diphenylacetic or α-napthylacetic acid, or a dibasic alkanoic acid, e.g., oxalic, maleic, fumaric, succinic, malonic, glutaric, α-methylglutaric, β-methylglutaric, β,β-dimethylglutaric, adipic, pimelic and suberic acid, a dibasic aryl acid, especially those capable of forming a cyclic anhydride, e.g., phthalic acid, or a carbamic acid, e.g., carbamic acid, phenylcarbamic, n-butylcarbamic, dimethylcarbamic, diethylcarbamic and allophanic acid; or of a heterocyclic acid, e.g., β-furylcarboxylic, pyrrolecarboxylic, β-pyrrolidylpropionic, N-methylpyrrolidyl-2-carboxylic, α-pincolinic, nicotinic, indole-2-carboxylic, 6-hydroxylindolyl-3-acetic and N-methylmorpholyl-2-carboxylic and pyrrolyl-2-carboxylic acid, or a sulfonic acid of 1 - 18, preferably 1 - 12 carbon atoms, including alkanesulfonic, e.g., methane- and ethanesulfonic, and aryl sulfonic, e.g., benzene- and p-toluenesulfonic acid.

Such contemplated equivalents can also be esters with an acid containing one, two or more simple substituents in the molecule, e.g., hydroxy, halo, alkoxy, acyloxy, sulfonyloxy, amido, sulfato, nitro, mercapto and cyano, in the molecule, e.g., glycolic, lactic, citric, tartaric, d-maleic, d-glyceric, mannoic, gluconic and salicylic acid; of an amino acid, e.g., glycine, aminopropionic, diglycollamic, triglycollamic, methylglycine, dimethylglycine, diethylglycine, para-aminosalicylic, paraaminobenzoic, ethylmercaptoacetic, benzylmercaptoacetic, chloroacetic, fluoroacetic, trichloroacetic, trifluoroacetic, thioglycolic, m-nitrobenzoic, 2,3,4-trimethoxybenzoic, phenoxyacetic and α-napthoxyacetic acid.

Norgestrel and its D- and L-entantiomers were tested in a placebo-controlled double blind experiment by quantitative pharmaco-electroencephalography (CEEG) and by the method of the evoked potentials on man (T.M. Itil et al, "Quantitative Pharmaco-Electroencephalography" [The Use of Computerized Cerebral Biopotentials in Psychltropic Drug Research] in "Psychotropic Drug and the Human EEG", Modern Problems of Pharmacopsychiatry Series, S. Karger, Basel-New York [1974].

Their effects and side effects were also determined by experimental-psychological investigations and with various rating scales, e.g., for neurological and psychosomatic symptomatology, by self-rating scales for sedation, anxiety, and depression, aswell as by interviews conducted by physicians.

The patients treated in the method of this invention are humans with a psychic disturbance of the affective and behavioral type, preferably those experiencing sleep disturbance and general restlessness, anxiety and/or tension, including also acute and chronic schizophrenics and those in states of mental depression.

The active agent, viz. norgestrel, its D-enantiomer, its L-enantiomer or a 17-ester of any of them, is administered in an amount effective to ameloriate or eliminate, viz., beneficially affect, the symptomology associated with the psychic disturbance.

Norgestrel, its enantiomers and their 17-esters can be utilized, for example, in the treatment of sleep disturbances, to induce sleep as well as sustain sleep, for the treatment of general unrest, states of anxiety and tension, also in acute and chronic schizophrenia, as well as states of depression.

Furthermore, the compounds employed in accordance with this invention are suitable for the treatment of restlessness and disturbances resulting from stress situations or excessive stimuli, as well as pathological aggressiveness.

The compounds employed in this invention are distinguished by the fact that they are not toxic and do not exhibit cataleptic side effects, i.e., they do not produce motoric disturbances.

A particular advantage of this invention is that no dependency or tolerance develops, even during long-term use, as is possible, for example, in case of the benzodiazepines.

The L-enantiomer of norgestrel and its esters thereof are especially suitable for the treatment of female patients, since the D-form and the racemate (norgestrel), due to their endocrinological activity, exhibit an undesired side effect. In male patients, all stereoisomers of norgestrel and/or the esters thereof can be administered.

The pharmaceutical compositions of this invention can be administered subcutaneously, intramuscularly, or orally, the desired effects being manifested upon parenteral as well as oral administration. The daily dosage is 0.05 – 500 mg., preferably 0.5 – 200 mg. per day, more preferably 3 – 25 mg. This dosage can be administered all at once or in several divided doses. The dosage range can, however, be greater or less, depending on the response of the individual patient and other medical considerations.

The pharmaceutical compositions of this invention are formulated in a conventional manner, viz., by processing norgestrel, its D- or L-enantiomer or one of their 17-esters, preferably an ester of 1 – 8 carbon atoms, together with carrier substances, diluents, flavor-ameliorating agents, etc., conventional in galenic pharmacy, into the desired form of administration, such as, for example, tablets, dragees, capsules, solutions, etc.

Particularly suitable for injections are oily solutions, such as, for example, solutions in sesame, castor or cottonseed oil. If desired, diluents or solubilizers can be added to increase the solubility, e.g., benzyl benzoate or benzyl alcohol. To achieve prolonged activity, the active agent can also be employed in microencapsulated form. Especially suitable for oral administration are capsules, tablets, dragees, pills, suspensions, emulsions, and solutions. The amount of active agent in the thus-formulated medicines per unit dosage is 0.05 – 100 mg., preferably 0.1 – 50 mg., and most preferably 1 – 25 mg.

The esters of norgestrel employed in accordance with this invention are prepared in accordance with conventional methods for esterifying steroids.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

50.0 mg. of $17\beta$-acetoxy-D-13-ethyl-$17\alpha$-ethynyl-4-gonen-3-one is mixed homogeneously with 110.5 mg. of lactose, 59.5 mg. of corn starch, 2.0 mg. of "Aerosil," 2.5 mg. of polyvinylpyrrolidone 25, and 0.5 mg. of magnesium stearate and compressed without previous granulation to round, biplanar tablets having a breaking notch and a final weight of 225 mg.

EXAMPLE 2

To produce an injection solution, 100.0 mg. of L-13-ethyl-$17\alpha$-ethynyl-$17\beta$-hydroxy-4-gonen-3-one is dissolved in 618.6 mg. of benzyl benzoate (USP XVII) and 353.4 mg. of castor oil (DAB 7, USP XVII); the solution is filtered under sterile conditions and filled into 3 ml.-ampoules under aseptic conditions.

EXAMPLE 3

Respectively 0.1 mg. of DL-13-ethyl-$17\alpha$-ethynyl-$17\beta$-hydroxy-4-gonen-3-one (micronized, particle size 2-8 $\mu$) is mixed homogeneously with 150 mg. of lactose (DAB 7, USP XVII) and filled into hard gelatin capsules (5 × 15 mm.).

EXAMPLE 4

Analogously to Example 1, 10 mg. of L-13-ethyl-$17\alpha$-ethynyl-$17\beta$-hydroxy-4-gonen-3-one is compressed, together with 110.5 mg. of lactose, 59.5 mg. of corn starch, 2.0 mg. of "Aerosil," 2.5 mg. of polyvinylpyrrolidone 25, and 0.5 mg. of magnesium stearate to tablets having a final weight of 185 mg.

EXAMPLE 5

Quantitative Pharmaco-Electroencephalography with D- and L- Norgestrel (A Placebo Controlled Double Blind Multiple Crossover - Latin Square Design - Study to Determine Drug Profile and Bioavailability)

In a controlled study, L-norgestrel, (2.5 mg., 10 mg. or 25 mg.), 2.5 mg. of D-norgestrel, and as a control drug placebo, 75 mg. of amitriptyline and 5 mg. of diazepam, were administered in a single oral dose to groups of 12 volunteers, each consisting of 6 male and 6 female, ranging in age from 21 to 45 years, in weekly intervals. The design was multiple crossover and double blind.

None of the drugs given produced any systematic and/or serious clinical or laboratory side effects. The results were obtained based on quantitative pharmaco EEG, as well as on chemical and psychological rating scales.

Based on multivariate randomized $T^2$-testers all dosages of L-norgestrel could be differentiated from placebo on a level of satistical significance.

The CEEG profiles of D- and L-norgestrel in all dosages given resembled the CEEG profiles of benzodiazepine anxiolytica and tricyclic antidepressants.

These results establish that D- and L-norgestrel each have systematic CNS-effects and will exhibit sedative and anxiolytic as well as antidepressive activity.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method for the treatment of psychic disturbances of the affective and behavioral type in humans, which comprises administering to a male patient manifesting such psychic disturbance an amount of DL-13-ethyl-17α-ethynyl-17β-hydroxy-4-gonen-3-one, or of the D-isomer only or of the L-isomer only, or a physiologically acceptable 17-ester thereof of a hydrocarbon carboxylic acid of 1 – 18 carbon atoms, effective to beneficially affect the symptomology associated with the psychic disturbance.

2. A method according to claim 1, wherein successive daily doses of 3 – 25 mg. per day are administered orally to the patient.

3. A method according to claim 1, wherein L-13-ethyl-17α-ethynyl-17β-hydroxy-4-gonen-3-one is administered to the patient.

4. A method for the treatment of psychic disturbances of the affective and behavioral type in humans, which comprises administering to a female patient manifesting such psychic disturbance an amount of L-13-ethyl-17α-ethynyl-17β-hydroxy-4-gonen-3-one or a physiologically acceptable 17-ester thereof of a hydrocarbon carboxylic acid of 1 – 18 carbon atoms, effective to beneficially affect the symptomology associated with the psychic disturbance.

5. A method according to claim 4, wherein successive daily doses of 3 – 25 mg. per day are administered orally to the patient.

6. A method according to claim 4, wherein L-13-ethyl-17α-ethynyl-17β-hydroxy-4-gonen-3-one is administered to the patient.

* * * * *